United States Patent [19]

Schäfer et al.

[11] 4,362,737
[45] Dec. 7, 1982

[54] TRANSDERMAL CARRIER MATERIALS

[76] Inventors: Rolf Schäfer, Grabenmattstrasse 37, 4133 Pratteln BL; Werner Schäfer, Auf der Wacht 33, 4104 Oberwil BL; Doris Schäfer, Neue Blauenrainstrasse 9, 4411 Arisdorf BL, all of Switzerland

[21] Appl. No.: 253,876

[22] Filed: Apr. 13, 1981

[51] Int. Cl.$^3$ ............... A61K 31/415; C07D 233/18
[52] U.S. Cl. ............... 424/273 R; 260/963; 548/112; 548/349; 548/354; 562/561; 562/565; 424/232; 424/266; 424/358
[58] Field of Search ............... 548/354, 112; 424/273 R

[56] References Cited
U.S. PATENT DOCUMENTS 4,267,350 5/1981 Tomalia et al. ............... 548/354

Primary Examiner—Richard A. Schwartz

[57] ABSTRACT

Amphoteric dissociating complexes which have a cationic group having the structure

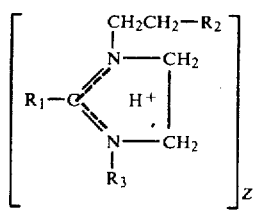

or

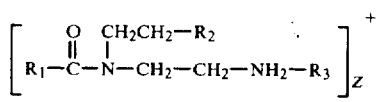

wherein:
$R_1$ is an aliphatic alkyl group having 6 to 22 carbons,
$R_2$ is a member of the group consisting of —$R_4$—(CH$_2$CH$_2$)—COOH, —$R_4$—(CH=CH)COOH and —OPO$_3$H$_2$, wherein $R_4$ is —NH—, —NH—CO—, or —O—CO—, and
$R_3$ is hydrogen, —CH$_2$—COOH or —CH$_2$—CH$_2$—COOH; and an anionic group which is either a carboxylate having the formula

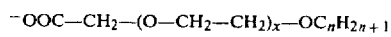

or a phosphate having the formula

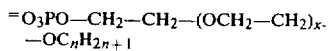

wherein:
n is 8 to 22 and x is 1 to 10; and z is 1 when the anionic radical is a carboxylate and z is 2 when the anionic radical is a phosphate are disclosed.

The compositions are effective carriers for active pharmaceutical or cosmetic ingredients. The active ingredients may be ionically complexed with the cationic or anionic group of the amphoteric complex or may be covalently bonded to one of the groups of the complex. Alternatively, the active substances may be transported in the carriers as micellar inclusions.

11 Claims, No Drawings

TRANSDERMAL CARRIER MATERIALS

BACKGROUND OF THE INVENTION (a) Field of the Invention

This invention relates to complexes useful as carriers for pharmaceutical and cosmetic active materials. The compositions permit continued constant rate transdermal penetration of active materials, that is through the cell membranes of skin and the gastrointestinal mucosa.

(b) State of the Art

Permeation of pharmaceutical and cosmetic active substances through body tissues when administered topically or orally is essential for effective treatment. Carrier materials for the active substances optimally should effect or permit penetration at a steady rate. Moreover, the carrier materials should not alter the cell membrane systems of the tissues or the proteins therein responsible for biochemical functions, such as substance transport.

Many surfactants or other strongly ionic materials which are used as penetration adjuvants, emulsifiers, wetting agents or the like in pharmaceutical or cosmetic compositions, as well as some strongly ionic active materials, alter the cell membrane, as by denaturing the membrane proteins, dissolving the lipid layer of the membrane or otherwise adversely affecting the membrane transport system. As a result, substance penetration is impeded or stopped and effective treatment is no longer achieved or excessively high doses are required to achieve the desired therapeutic effect.

It has now been discovered that these problems can be overcome and relatively steady and unhindered permeation of active materials through body tissues can be achieved by inclusion of the active material in a complex amphoteric compound.

SUMMARY OF THE INVENTION

This invention relates to amphoteric dissociating complexes which are useful as transdermal carriers or pharmaceutical active ingredients. The complexes have a cationic group having the structure

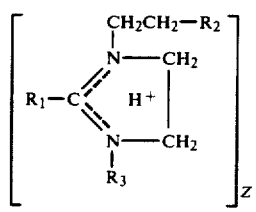

or

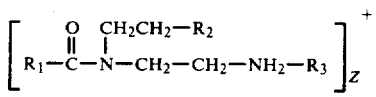

wherein:

$R_1$ is an aliphatic alkyl group having 6 to 22 carbons,
$R_2$ is a member of the group consisting of $-R_4-(CH_2CH_2)-COOH$, $-R_4-(CH=CH)COOH$ and $-OPO_3H_2$, wherein $R_4$ is $-NH-$, $-NH-CO-$, or $-O-CO-$, and
$R_3$ is hydrogen, $-CH_2-COOH$ or $-CH_2-CH_2-COOH$; and an anionic group which is either a carboxylate having the formula

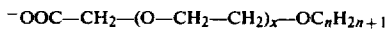

or a phosphate having the formula

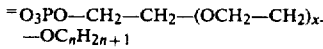

wherein:

n is 8 to 22 and x is 1 to 10; and Z is 1 when the anionic radical is a carboxylate and Z is 2 when the anionic radical is a phosphate. The complexes enhance permeation through skin membranes of active pharmaceutical or cosmetic ingredients incorporated therein.

DETAILED DESCRIPTION OF THE INVENTION

The present invention provides carriers for active pharmaceutical and cosmetic ingredients. The carriers are amphoteric-dissociating complexes which are metabolized in a manner whereby substantially unhindered permeation through cell membranes is achieved.

The amphoteric-dissociating complexes of the invention have a cationic group of the formula

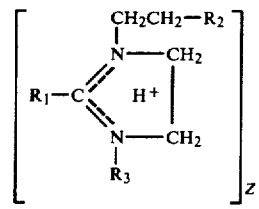

or

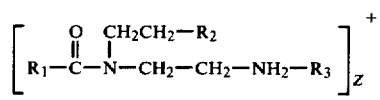

wherein:

$R_1$ is an aliphatic alkyl group having 6 to 22 carbons,
$R_2$ is a member of the group consisting of $-R_4-(CH_2CH_2)-COOH$, $-R_4-(CH=CH)COOH$ and $-OPO_3H_2$, wherein $R_4$ is $-NH-$, $-NH-CO-$, or $-O-CO-$, and
$R_3$ is hydrogen, $-CH_2-COOH$ or $-CH_2-CH_2-COOH$; and an anionic group which is either a carboxylate having the formula

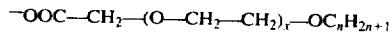

or a phosphate having the formula

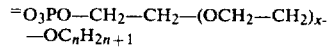

wherein:

n is 8 to 22 and x is 1 to 10; and Z is 1 when the anionic radical is a carboxylate and Z is 2 when the anionic radical is a phosphate. Also included within the scope of the invention are the alkali metal salts, such as potassium and sodium salt formed with the carboxylate or phosphate groups of the cationic group.

Preferred complexes of the invention are those having the above cationic imidazoline group, wherein $R_1$ is $C_{12}H_{25}$ or, less preferably, the alkyl residues of capryl, cocoyl, oleyl, palmitoyl, stearyl or behenyl fatty acids, $R_2$ is $-NH-CH_2-CH_2COOH$ or, less preferably, one of the above other groups and $R_3$ is $-CH_2-CH_2-COOH$ or, less preferably, one of the other defined groups, complexed with the above carboxylate anionic groups wherein x is 5 and n is 12.

The complexes of the invention may be prepared by treating alkali metal salts of an imidazoline with a carboxylic or phosphoric acid in aqueous solution, said reactants having structures corresponding to those defined above for the cationic and anionic radicals. Stoichiometric amounts of the reactants may simply be stirred at 20°-80° C., preferably 40° C. for about 15 minutes, to form the complex. Complex formation has been verified by high voltage electrophoresis and column chromatography.

Ring closure of imidazoline reactants necessary to form of the complexes of the invention may be effected by reacting an appropriate carboxylic acid with an appropriate di- or triamine according to the following exemplary reaction sequence:

$$R_1-COOH + R_5-CH_2CH_2NHCH_2CH_2NH_2 \xrightarrow[20 \text{ mm Hg}]{180° \text{ C., 6 hrs.}}$$

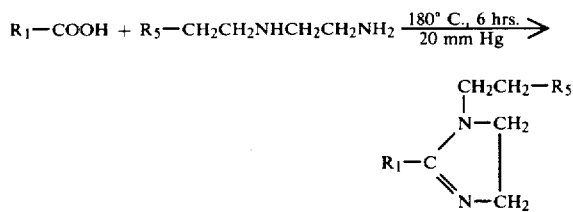

wherein $R_5$ is an hydroxyl, chloride or amino group and $R_1$ is as defined above. The resulting ring compound may then be reacted with $CH_2=CH_2-COOH$ or chloracetic acid at 120° C. for 4 hours to provide the corresponding $R_3$ substituent.

The $R_2$ substituents may be incorporated into the compounds (1) by dissolving the ring material in a solvent, such as chloroform or methylene chloride, and adding with stirring at room temperature acrylic acid or a suitable anhydride; (2) by dissolving the ring material in aqueous solution and reacting with an appropriate amino acid at 50°-80° C. for one hour; or (3) by stirring the ring material into polyphosphoric acid at 60° C. for 1 hour.

Where $R_3$ is hydrogen, the open ring reactants used to form the cationic group of the complexes of the invention can be formed by hydrolysis of the imidazoline compounds in aqueous solution at pH 9 for two hours at 60° C. Where $R_3$ is not hydrogen the ring is hydrolyzed prior to substitution at the $R_3$ position. The anion reactants are available commercially or may be formed by conventional techniques.

Active cosmetic or pharmaceutical ingredients can be incorporated into the complexes of the invention to thereby facilitate transport of the active through tissue membranes. Where the active material itself can exist as an ionic radical of the type which can react to form a salt with the complex of the invention, incorporation can be achieved by simply reacting the active material with the complex. For example, a carboxylate active ingredient could be reacted with a complex having a cationic group in sodium salt form.

Active materials which do not contain ionic groups suitable for salt formation can be incorporated into the complexes of the invention by covalent bonding to one or the other complex substituent. Active materials can also be incorporated into the complexes of the invention by micellar inclusion or secondary bonding, i.e., Van der Waal's forces and electrostatic interaction.

The substituents of the cationic portion of the complexes of the invention are those which are metabolized into physiologically acceptable materials. This is believed to account, in part, for the suitability of these materials for skin transport vehicles. It is further postulated that the complexes of the invention are effective cell membrane transport vehicles due to their amphoteric resemblance to lipids and membrane proteins responsible for substance transport. Moreover the complexes appear to have relatively little or at least delayed denaturing effects on the membrane proteins and do not appear to change the protein configuration or solubilize the lipid layer of the cell membranes. It is believed that the complexes of the invention have minimal adverse effects on cell metabolism and, more specifically, the membrane transport system necessary therefor, due to these characteristics.

Where an active ingredient is strongly ionic or itself contains substituents which produce adverse effects on cell membranes, it may be rendered physiologically more compatible and transport thereof can be further enhanced by reacting the active with glutamic acid, aspartic acid, lysine or arginine to form a salt in addition to combining the active with a complex of the invention. Such salts mask the physiologically adverse effects of the active ingredient. Further, where high levels of active must be administered, nicotinic cid or acetylsalicylate may be reacted to form salts or complexes with the imidazoline or active material. Such salts produce hyperaemia, thus enhancing absorption of the active materials. Other hyperaemia inducing salts may also be employed.

The complexes along with effective amounts of the active ingredients are formulated as a bath, cream or other composition for topical application or into a composition for oral administration. Such formulations generally are aqueous based. In addition to the water base, carrier complex and active ingredient, other materials commonly employed in topical or oral pharmaceutical or cosmetic compositions may be included in the formulations. For example, preservatives, antimicrobials, foaming agents or the like can be employed. Surfactants, particularly sulfate surfactants, which inhibit membrane transport, should be avoided.

The following examples are illustrative of the invention.

EXAMPLE 1

A preferred formulation for use in application of active ingredients in a bath contains a complex having the structure

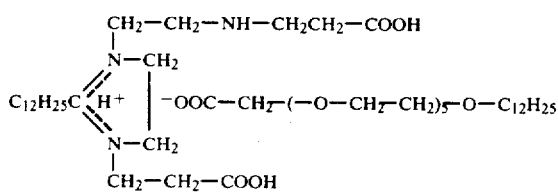

This complex is preferably applied in a composition containing:

Complex: 15 parts
Cocofattyacid diglycolamide: 3 parts
Stearyl alcohol decaoxethylate: 9 parts
Isopropanol: 5 parts
4-Hydroxybenzoicacidmethylester: 0.2 parts
4-Hydroxybenzoicacidpropylester: 0.1 part
and sufficient active ingredient and water to bring the total composition to 100 parts.

EXAMPLE 2

A preferred complex for use in a cream formulation has the structure

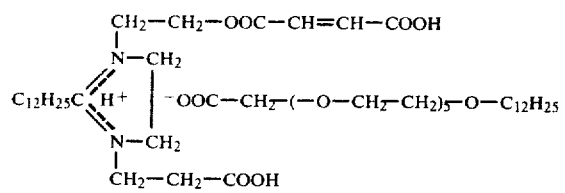

In addition, the cream preferably contains a salt of nicotinic acid and the imidazene group of the complex employed in Example 1 to induce hypanemia in the skin to which the cream is applied. The composition of a cream preferably is as follows:

Complex: 5%
Glyceryltricocoate: 38.5%
Glyceryltricaprylate: 5%
Vitamineoil (germ oils): 2.5%
Lanolin: 1%
Nicotinic salt: 1.5%
Glycerol: 4%
Ascorbic acid: 3%
4-Hydroxibenzoicacidmethylester: 2%
4-Hydroxibenzoicacidpropylester: 1%
and sufficient active ingredient and water to yield 100%.

EXAMPLE 3

A formulation for oral administration preferably contains a complex of the structure

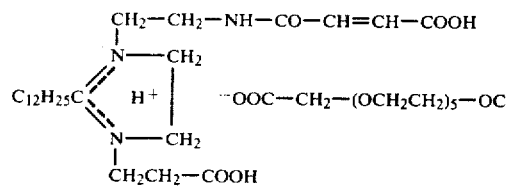

The complex is added to a formulation of the following composition:

Complex: 0.2%
Phosphatidylcholin: 0.5%
Taurocholic acid-Na salt: 1.9%
Vitamin oil (germ oil): 12.5%
4-Hydroxybenzoicacidmethylester: 0.2%
4-Hydroxybenzoicacidpropylester: 0.01%
and active ingredient and water sufficient to total 100%.

EXAMPLE 4

Three complexes in accordance with the invention were formed and their effects on skin penetration of five essential oils was compared with the penetration effects of a conventional sulfate surfactant mixture.

The first formulation contained two complexes. The first was prepared from 2-aliphatic alkyl-1-beta-hydroxyethyl-1-carboxymethyl imidazoline and dodecyl-pentaoxethyl glycolic acid ether (Complex I) while the second was prepared from aliphatic alkyl polypropylene-polyamino-polypropionic acid and n-octylmonophosphoric acid ester (Complex II). The reactions were effected at 60° C. by adding to a 50% aqueous solution of the imidazoline and the propionic acid derivative respectively a 50% aqueous solution of the second reactant at 60° C. The addition was accomplished with stirring which was continued until a pH of 7.2 and 6.8 were achieved in the first and second reaction solutions respectively. The complexes were incorporated into formulation 1 as follows:

|  | Weight % |
| --- | --- |
| 50% aqueous solution Complex I | 27% |
| 50% aqueous solution Complex II | 27% |
| Lanic acid isopropanolamide | 3 |
| 1,3-Butylene glycol | 3 |
| Water | 20 |
| Ethereal Oils | 20 |

Formulation 2 contained Complex III formed from 2-aliphatic alkyl-1-beta-hydroxyethyl-1-carboxymethyl imidazoline and coconut alkyl carbonamido-ethyl-aminoacetic acid and Complex IV prepared from stearylcarbonamido-tripropylene-triaminodipropionic acid betaine and mono-/dioleyl-sorbitanester monophosphoric acid. The complexes were formed employing molar amounts of each reactant and the conditions employed to form Complex I. Formulation 2 was as follows:

|  | Weight % |
| --- | --- |
| 50% aqueous solution Complex III | 27 |
| 50% aqueous solution Complex IV | 27 |
| Lauric acid isopropanolamide | 3 |
| Isopropylalcohol (cosmetic grade) | 3 |
| Water | 20 |
| Ethereal Oils | 20 |

The third test formulation was an emulsion which contained Complex V formed from 2-aliphatic alkyl-1-beta-hydroxyethyl-1-carboxymethyl imidazoline and Myristin alcohol-nonaoxethyl ether-phosphoric acid ester. Complex V was prepared by combining 0.6 gram of the imidazoline as 100% anhydrous product and 1.2 gram of the phospate ester at 60° C. A pasty product was obtained which formed a clear solution in the formulation below. Formulation III was as follows:

|  | Weight % |
| --- | --- |
| Complex V | 1.8 | and diluted with 5 ml H$_2$O. This dilution corresponds to a normal bath formulation containing 0.02% bath concentrate, corresponding to 20 ml per 100 liter bath water. The results are set forth in Table I:

TABLE I

| | | (ng active substance per 100 l blood) | | | | |
|---|---|---|---|---|---|---|
| | Penetration time (min.) | Alpha-pinene | Methanol | Isobornyl acetate | Limonene | Camphor |
| Formulation 1 | 5 | 1.05 | 1.5 | 2.8 | 2.7 | 4.7 |
| | 10 | 2 | 2.7 | 5.9 | 5.8 | 7 |
| | 20 | 2.9 | 3.6 | 6.5 | 6.6 | 9.1 |
| | 40 | 3.4 | 4.2 | 6.9 | 7.2 | 10.8 |
| Formulation 2 | 5 | 1.1 | 1.6 | 12.6 | 2.8 | 4.6 |
| | 10 | 2.3 | 2.6 | 5.8 | 5.9 | 6.7 |
| | 20 | 2.8 | 3.7 | 6.4 | 6.7 | 8.9 |
| | 40 | 3.9 | 4.1 | 7.1 | 7.3 | 10.3 |
| Formulation 3 | 5 | 1.3 | 1.2 | 2.5 | 2.8 | 4.2 |
| | 10 | 2.7 | 2.6 | 5.3 | 5.9 | 7.1 |
| | 20 | 3.5 | 3.4 | 6.2 | 6.3 | 8.8 |
| | 40 | 4.2 | 4.0 | 6.8 | 7.1 | 10.9 |
| Formulation 4 | 5 | 1.1 | 0.9 | 1.8 | 1.7 | 2.9 |
| | 10 | 2.1 | 1.8 | 3.3 | 3.4 | 2.7 |
| | 20 | 0.6 | 1.2 | 1.8 | 2.1 | 2.3 |
| | 40 | 0.3 | 0.7 | 0.9 | 1.1 | 1.2 |

-continued

| | Weight % |
|---|---|
| Amphosurfactant of the type lauric acid amidopropyl dimethylaminoacetic acid betaine (30% aqueous solution) | 10 |
| Mixture of oleyl alcohol and saturated fat alcohols C$_{12-14}$ | 8.6 |
| Capric/caprylic acid triglyceride | 2.5 |
| Isopropyl myristate | 2.2 |
| Plant oil with 70% iso-linolic acid triglyceride | 2.2 |
| Distilled lanolin fraction | 1.4 |
| Mixture of fatty acid mono- to tri-sorbitan esters | 3.9 |
| Fat alcohol-octapolyoxethyl fatty acid ester | 0.8 |
| Lauryl polydiethanolamide | 2.9 |
| Water | 43.7 |
| Ethereal Oils | 20 |

The sulfate surfactant formulation was as follows:

| | Weight % |
|---|---|
| Lauryl-3,5-polyoxethylether sulfate-sodium salt (40% aqueous solution) | 40 |
| Lauryl-N—methyltaurid-sodium salt (40%) | 20 |
| Lauric acid-diethanolamide (100%) | 6 |
| Isopropanol | 3 |
| Water | 11 |
| Ethereal oils | 20 |

To test their penetration and permeation effects, the complex-containing formulations were applied in bath form. The formulations, identified with radioactively marked essential oils, were applied to dd mice. The dd mice were shaved on the back and placed in a retention tube with external air supply. A cyinder having a silicone soft seal and a gas-proof cover was sealed on the shaved area. The cylinder had a base area of 3 cm$^2$.

After filling the cylinder with 5 ml of a radioactively marked formulation, 100 microliters of blood was taken from the tail vein of the animals at various intervals and the radioactivity was determined. At the same time another blood aliquot was admixed with 1 mg of the corresponding unmarked component, the mixture re-extracted with suitable solvents and the active substance chromatographed on thin layer plates, to determine by a suitable staining method the percentage of radioactivity in the blood aliquot which had been transformed into other products by metabolization of the active substance.

Bath formulations were as follows:

To each $\mu$g (3.3.-6.1 $\times$ 10$^7$ dpm) of the labeled substance 1 $\mu$l (=1 mg) of the bath concentrate was added

EXAMPLE 5

The test formulations were repeated as in Example 1 using the pure complex or surfactant mixture without active substance. The pure complex or surfactant mixtures were applied to the skin for 5, 10, 20 or 40 minutes and thereafter were replaced for 10 minutes by the corresponding surfactant mixture with $^3$H-menthol. Table II sets forth the results:

TABLE II

| | Preincubation time with surfactant mixture | ng menthol/100/ul blood after 10 minutes |
|---|---|---|
| Formulation 1 | 5 | 2.4 |
| | 10 | 2.6 |
| | 20 | 2.5 |
| | 40 | 2.6 |
| Formulation 2 | 5 | 2.3 |
| | 10 | 2.5 |
| | 20 | 2.6 |
| | 40 | 2.4 |
| Formulation 3 | 5 | 2.5 |
| | 10 | 2.5 |
| | 20 | 2.4 |
| | 40 | 2.4 |
| Formulation 4 | 5 | 1.7 |
| | 10 | 1.3 |
| | 20 | 1.1 |
| | 40 | 0.6 |

The results indicate formulations 1 to 3 do not affect the skin transport mechanism, while formulation 4 inactivates the transport mechanism.

EXAMPLE 6

40$\mu$ Ci each of $^{35}$S-heparin-Na salt was incorporated in 100 mg ointment base with 20% formulation 4 or surfactant mixture 2 of Example 4, $^{35}$Sheparin-arginyl salt in 100 mg ointment base with 20% formulation 2 or formulation 4 and $^{35}$S-heparin arginyl salt in 100 mg ointment base with 20% formulation 3. The specific activity was 100$\mu$ Ci/mg. 50 mg portions of the ointments were applied to a 15 cm$^2$ shaved skin area of dd mice. After 120 minutes application time, the skin was wiped off several times with absorbent cotton and the horny layer removed by Scotch tape tearoffs. From the horny layer free skin excisate a 50-mm$^2$ stamping was taken and cut horizontally in the freeze microtome. The first layer of a thickness of 100 micron was designated as epidermis and the remaining 100 micron thick layer as corium.

To the cut skin pieces were added 1 mg unmarked heparin and the tissue was homogenized in physiologic salt solution. Then heparin was extracted from these aliquots with cetyltrimethyl-ammonium bromide and the product centrifuged in sucrose gradients. The radioactivity, which co-sedimented with heparin fractions with molar weight of 12,000 to 16,000 corresponded to the pentrated, not metabolized quantity of $^{35}$S-heparin. The values are given in Table III:

TABLE III

| Application form | | I.U. penetrated heparin calculated for 1 cc tissue |
|---|---|---|
| Heparin-Na salt in Formulation 4 | Epidermis | 0.40 |
| | Corium | 0.02 |
| Heparin-arginyl salt in Formulation 2 | Epidermis | 17.2 |
| | Corium | 0.9 |
| Heparin arginyl salt in Formulation 3 | Epidermis | 19.4 |
| | Corium | 1.1 |
| Heparin-Na salt in Formulation 2 | Epidermis | 0.35 |
| | Corium | 0.03 |
| Heparin-arginyl salt in Formulation 4 | Epidermis | 2.7 |
| | Corium | 0.18 |

1000 I.U. heparin-Na salt were incorporated in 500 mg ointment base with formulation 3 or 1000 I.U. heparin-Na salt in 500 mg ointment base with formulation 4.

Groups of 10 male rats (150 g/animal) received intraduodenally 0.5 ml of the formulation with mixture 3 (a), 0.5 ml of the formulation with surfactant mixture 4 (b), 1000 I.U. heparin-Na salt in 0.5 ml H$_2$O (c) or formulation (a) and (b) without heparin (d) and (e). Thirty minutes after administration of the preparations, the amount of heparin penetrated in the intestine was determined by measuring the coagulation time of the blood of the treated animal:

| Groups | a | b | c | d | e |
|---|---|---|---|---|---|
| Blood coagulation time (min.) | 60 | 2.4 ± 0.2 | 2.0 ± 0.2 | 2.7 ± 0.3 | 1.8 ± 0.3 |

EXAMPLE 7

$^{14}$C-marked chloracetyl-pantothenylol was reacted with an excess (5 equivalents( of lysin. The reaction product (20μ Ci $^{14}$C-marked lysil-glycyl-pantothenylol) was incorporated in 100 mg ointment base with 20% formulation 3 or 4. As a reference $^3$H-marked pantothenylol was incorporated in 100 mg ointment base with 20% formulation 3 or 4. The epidermal application occurred as in Example 6. For the evaluation of the two radioactively marked active substances, the activity was determined after 60 minutes in the epidermis and corium by scintillation count. The values are given in the following table:

TABLE IV

| Application form | | |
|---|---|---|
| Arginyl-glycyl-pantothenylol in surfactant mixture 3 | Epidermis | 4.3 μg |
| | Corium | 0.38 μg |
| Arginyl-glycyl-pantothenylol in surfactant mixture 4 | Epidermis | 1.7 μg |
| | Corium | 0.11 μg |
| Pantothenylol in surfactant mixture 3 | Epidermis | 0.33 μg |
| | Corium | 27 ng |
| Pantothenylol in | Epidermis | 0.9 μg |

TABLE IV-continued

| Application form | | |
|---|---|---|
| surfactant mixture 4 | Corium | 40 ng |

EXAMPLE 8

The effects of the formulations on the growth of the skin flora and primary human epithelium cells was tested. A skin smear of human epidermis was made with a sterile millipore filter and was grown overnight. The next day the bacteria were diluted to 10$^8$ cells/ml (early logarithmic phase) and shaken at 37° C. in nutrient broth without formulation (control) and with various dilutions of the formulation in the medium. The generation time was observed optically by turbidity measurement at 610 nm. The obtained growth curves and the generation times calculated therefrom correspond to the mean values of 3 cultures each. The standard deviation was ±3%. The results are set forth in Table V.

Portions of 5×10$^5$ primary human epithelium cells were seeded in 15 cm$^2$ cell culture bottles, that is 1/10 confluence. After incubation for 4 hours in Eagle's full medium with 10% calves' serum, the surfactant mixtures were added to the media in different dilutions and incubated at 37° C. Thereafter the cells were trypsinized after different times, vital stained, and counted in a counting chamber. The obtained growth curves and the generation times calculated therefrom corresponded to the mean values from 5 cultures each per measuring point. The standard deviation was ±5%. Results are set forth in Table VI.

Generation time > means complete inactivation of the cells.

TABLE V

| | Generation time (hours) | | | |
|---|---|---|---|---|
| % Surfactant in the medium | 1 | 2 | 3 | 4 |
| 0 (control) | | (0.75) | | |
| 0.001 | 0.75 | 0.75 | 0.75 | 0.75 |
| 0.01 | 0.75 | 0.75 | 0.75 | 0.75 |
| 0.02 | 0.75 | 0.75 | 0.75 | 2.8 |
| 0.05 | 0.75 | 0.75 | 0.75 | ∞ |
| 0.1 | 1.5 | 1.5 | 0.75 | ∞ |
| 0.2 | 3.5 | 3.5 | 0.75 | ∞ |
| 0.5 | ∞ | ∞ | 0.75 | ∞ |
| 1 | ∞ | ∞ | 1.5 | ∞ |

TABLE VI

| 0 (control) | | (19) | | |
|---|---|---|---|---|
| 0.005 | 19 | 19 | 19 | 44 |
| 0.01 | 46 | 48 | 19 | 135 |
| 0.02 | 320 | 310 | 115 | ∞ |
| 0.05 | ∞ | ∞ | ∞ | ∞ |

0.02% surfactant mixture in the medium corresponds to a typical dilution in formulating a full bath.

We claim:
1. An amphoteric-dissociating complex having
   (a) a cationic radical having the formula:

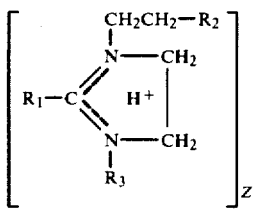

wherein:

$R_1$ is an aliphatic alkyl group having 6 to 22 carbons, $R_2$ is a member of the group consisting of $-R_4-(CH_2 \quad CH_2)-COOH$, $-R_4-(CH=CH)COOH$ and $-OPO_3H_2$, wherein $R_4$ is $-NH-$, $-NH-CO-$, or $-O-CO-$, and $R_3$ is hydrogen, $-CH_2-COOH$ or $-CH_2-CH_2-COOH$; and (b) an anionic group having the formula $-OOC-CH_2-(O-CH_2-CH_2)_x-OC_nH_{2n+1}$ wherein:

n is 8 to 22 and x is 1 to 10; and Z is 1.

2. An aqueous based pharmaceutical or cosmetic composition comprising a complex of claim 1 and an active ingredient.

3. The complex of claim 1 wherein $R_1$ is a $C_{12}H_{25}$ radical, $R_3$ is a $CH_2CH_2COOH$ radical, x is 5 and n is 12.

4. The complex of claim 3 wherein $R_2$ is NH—CH$_2$—CH$_2$—COOH.

5. A bath pharmaceutical or cosmetic formulation comprising the complex of claim 4 as a carrier and an effective amount of an active ingredient.

6. The complex of claim 3 wherein $R_2$ is a OOC—CH=CH—COOH radical.

7. A cream pharmaceutical or cosmetic formulation comprising the complex of claim 6 as a carrier and an effective amount of an active ingredient.

8. The complex of claim 3 wherein $R_2$ is a NH—CO—CH=CH—COOH radical.

9. An oral pharmaceutical or cosmetic formulation comprising the complex of claim 8 as a carrier and an effective amount of an active ingredient.

10. The formulaton of claims 5 or 7 further comprising a hyperaemia inducing salt.

11. The formulation of claims 5, 7 or 9, wherein the active ingredient is formulated with a member of the group consisting of glutamic acid, aspartic acid, lysine and arginine.

* * * * *